United States Patent [19]

Abrutyn

[11] Patent Number: 5,173,535
[45] Date of Patent: Dec. 22, 1992

[54] PLASTICS CONTAINING SUSTAINED RELEASE OF FUNCTIONAL MATERIALS

[75] Inventor: Eric S. Abrutyn, Middletown, N.Y.

[73] Assignee: Dow Corning Corporation, Midland, Mich.

[21] Appl. No.: 154,910

[22] Filed: Feb. 11, 1988

[51] Int. Cl.$^5$ ............................................. C08G 63/48
[52] U.S. Cl. ................................... 525/54.3; 525/191; 525/225; 525/239; 525/240; 525/241
[58] Field of Search ................ 524/525; 525/240, 241, 525/54.3, 225, 239, 191

[56] References Cited

U.S. PATENT DOCUMENTS

| | | | |
|---|---|---|---|
| 3,857,932 | 12/1974 | Shepherd et al. | 424/19 |
| 4,202,880 | 5/1980 | Fildes et al. | 424/78 |
| 4,291,980 | 9/1981 | Patterson | 356/243 |
| 4,309,509 | 1/1982 | Wood | 521/132 |
| 4,339,550 | 7/1982 | Palinczar et al. | 521/99 |
| 4,587,129 | 5/1986 | Kliment | 426/534 |
| 4,590,111 | 5/1986 | Takeuchi | 428/67 |
| 4,724,240 | 2/1988 | Abrutyn | 514/847 |
| 4,788,164 | 11/1988 | Che et al. | 501/39 |
| 4,906,694 | 3/1990 | Yonekura et al. | 525/240 X |
| 5,008,332 | 4/1991 | Sano et al. | 525/240 X |

FOREIGN PATENT DOCUMENTS

| | | |
|---|---|---|
| 0061701 | 10/1982 | European Pat. Off. . |
| 0252463 | 1/1988 | European Pat. Off. . |
| 0201214 | 11/1988 | European Pat. Off. . |

*Primary Examiner*—Joseph L. Schofer
*Assistant Examiner*—J. M. Reddick
*Attorney, Agent, or Firm*—Eckert Seamans Cherin & Mellott

[57] ABSTRACT

Plastic materials having distributed therein discrete particles of crosslinked polymers having functional material entrapped within the polymer lattices during the in situ polymerization of the monomers forming the polymer for the purpose of a controlled release of the functional material.

4 Claims, No Drawings

PLASTICS CONTAINING SUSTAINED RELEASE OF FUNCTIONAL MATERIALS

FIELD OF THE INVENTION

The present invention relates to novel plastic materials having distributed therein discrete particles of crosslinked polymers having entrapped therein functional materials. More particularly, the discrete particles have functional material entrapped therein among the polymer lattice during the in situ polymerization of the monomers forming the polymer for the purpose of a controlled release of the functional material.

BACKGROUND OF THE INVENTION

Application Ser. No. 683,603 filed Dec. 12, 1984, and now U.S. Pat. No. 4,724,240 which is herewith incorporated by reference, discloses solid compositions wherein a functional group is entrapped in the lattice of a crosslinked hydrophobic polymer during in situ polymerization of the monomers forming the polymer lattice.

U.S. Pat. No. 4,587,129 of Kliment, which is incorporated herein by reference, discloses a solid slow release hydrogel composition consisting of a flavor or a fragrance entrapped in a hydrophilic copolymer.

It is known to impregnate plastic articles having a high porosity with materials that have medicaments, volatile germicides, disinfecting agents, and the like. Such materials are generally polymeric carriers as disclosed in U.S. Pat. Nos. 3,857,932 and 4,202,880.

U.S. Pat. No. 4,339,550 of Palinczar relates to the incorporation of volatile materials into hydrophilic polyurethane foam for purposes of a sustained release of the materials.

U.S. Pat. No. 4,309,509 of Wood discloses an odorant containing foam prepared by reacting a prepolymer with an aqueous reactant containing a volatile odorant which is diffused into the air.

U.S. Pat. No. 4,590,111 of Takeuchi discloses a fragrance releasing sheet article having a pattern member which is formed of a thermoplastic or thermosetting resin and a fragrance releasing member composed of a thermoplastic or thermosetting resin and perfume.

Styrene-divinylbenzene copolymer, which is one crosslinked polymer that is useful in the practice of the present invention, can be prepared as described in U.S. Pat. No. 4,291,980 of Patterson or the article of Patterson entitled, "Preparation of Cross-Linked Polystyrenes and Their Derivatives for Use as Solid Supports or Insoluble Reagents" in *Biochemical Aspects of Reaction on Solid Supports*, Stark, ed. Academy Press, pp. 189-213, 1971.

Attempts have been made in the past to incorporate high levels of functional components into thermoplastic and thermoset resins. However, high levels of functional materials incorporated into resins usually results in the sacrifice of beneficial physical properties. Polystyrene cannot tolerate fragrances or similar compounds because of the negative effect on mechanical properties. Polyolefins and polyvinyl chloride can only tolerate low levels before dramatic distortions on the mechanical properties are experienced. Polyurethanes have been successfully foamed in situ in combination with fragrances and biocides. However, the number of functional groups which may be incorporated is limited because of side reactions with some functional materials during the foaming process.

The art is replete with attempts to render functional materials amenable to release on demand when incorporated in a resinous material. Encapsulation confines materials in discrete units or capsules as a result of coating particles of the material with an encapsulant. The coating wall or encapsulating material used in encapsulation includes natural or synthetic polymers which permit release of the functional material by fracture, degradation, or diffusion. A uniform sustained release of the functional material is not usually possible.

The incorporation of more than one functional component into plastic materials can result in problems during manufacturing since the high temperatures that the plastics are worked could cause loss or reaction of the functional components and deactivation for their intended purposes. Melt spinning or casting of synthetic fibers is one of such instances where functional components may volatilize or react with functional end groups of the polymer.

OBJECTS OF THE INVENTION

It is an object of the present invention to provide a means for incorporating into thermoplastic or thermosetting resinous material functional material without substantially affecting the mechanical properties of the resin or that of the functional material.

It is a further object of the present invention to incorporate into thermoplastic or thermosetting resins which can be foamed, cast, molded, spun into filaments, and the like, functional material capable of sustained release which can have a large variety of use.

It is a still further object of the invention to provide a means for incorporating into resinous material volatile functional components so as to reduce their loss during working of the resinous material at elevated temperatures.

It is a yet still further object of the invention to provide a foamed plastic article having incorporated therein functional materials capable of sustained release over a long period of time.

It is also an object of the invention to provide a means for releasing functional material, such as a medicament from a polymeric material only when required by an aqueous medium or body fluids.

It is an object of the invention to provide a pad which can utilized alone or in combination with other materials which comes into contact with the human body so as to eliminate odors and retard the formation of bacteria or virus.

These and other objects, which will become apparent from a reading hereinafter, and obtained from a thermoset or thermoplastic resin having incorporated therein discrete particles of crosslinked polymers having functional material entrapped amongst the polymer lattices during the in situ polymerization of the monomers forming the polymers.

SUMMARY OF THE INVENTION

It has now been found that a relatively high amount of functional material can be incorporated into thermoplastic or thermosetting resins without any substantial reduction in mechanical properties of the resin by first entrapping the functional material within the polymer lattices of a separate crosslinked polymer to form discrete particles prior to incorporation into the resin. The crosslinked polymer and functional material comprises discrete particles formed by the in situ polymerization of the monomers forming the polymer together with the functional material whereby the functional material is entrapped within the polymer lattice. The crosslinked polymer may be hydrophobic or hydrophilic depending upon the reasons for incorporation and the ultimate use of the final polymer. Preferably, the discrete particles comprise about 3% to about 50% by weight of the total polymer composition.

The crosslinked polymers which can be utilized are soluble, linear or branched copolymers or crosslinked insoluble polymers. According to the structure and chemical properties of the crosslinked polymers, heterogeneous or homogeneous entrapment can occur. Homogeneous or heterogeneous entrapment is also dependent on the structure and the amount of the crosslinker, where higher crosslinking density results in heterogeneous products. The amount of crosslinker can vary from 0.01 to 99.99 mul percent.

The functional materials which may be incorporated into the lattices of the crosslinked polymer depend upon the ultimate use of the final product. The functional materials may include fragrances, pharmaceuticals, dyes, biocides, pigments, pesticides, insect repellants, etc.

The polymers in which the particles of crosslinked polymers having the entrapped functional material may be incorporated are any thermoplastic or thermosetting resin. The polymers may be molded, cast or spun into fiberous materials depending upon the use of final product. Surprisingly, the polymer forming the particles provides a thermal barrier so that there is substantially no loss of functional material even at high temperatures. The entrapped functional material may also be incorporated into polyurethane foams during its preparation. The functional material therein may be, for example, a fragrance or a biocide for use in a foam product such as for forming bed and seat pads for patients, sponge mops, and vaginal devices which are constructed of open celled polymeric foam for the incorporation therein of contraceptive materials.

Suitable thermoplastic and thermosetting plastic materials include polyolefins, polyesters, Novolak resins, cellulose acetate, phenolic resins, polyurethane acrylic polymers, etc. The plastic materials can comprise the same or different polymers as the discrete particles which are incorporated therein.

The invention is especially useful in connection with the preparation of synthetic paper or fibers which may be utilized in the manufacture of diapers, catamenial pads, and the like. Advantageously, the functional material is incorporated into the fibers according to the present invention during the preparation of the base materials. The functional material may be a fragrance or a biocide which is continuously released or rapidly released by the action of the body fluids on the polymer in which it is entrapped.

The invention is further useful for providing fragrances for cast polymeric systems. For example, a leather-like fragrance can be entrapped within a suitable crosslinked polymer and the powder or beads formed thereby may be added to polyvinyl chloride prior to extrusion when forming artificial leather or the like.

PREPARATION OF SOLID LATTICE-ENTRAPPED COMPOSITIONS

The solid lattice-entrapped compositions utilized in this invention are prepared by combining in one step a functional crosslinking monomer, a monofunctional monomer and the functional material to be entrapped within the lattice under such conditions as to thereafter initiate polymerization. As used herein, the term "functional crosslinking monomer" is meant to include di- or polyfunctional monomers having two or more polymerizable double bonds, while the term "monofunctional monomer" is meant to include a polymerizable monomer having one double bond. Functional crosslinking monomers useful in the invention may be a polyunsaturated monomer selected from the group consisting of a mono- or di-ester of an alcohol and an alpha-beta unsaturated carboxylic acid; polyunsaturated polyvinyl ether or a polyhydroxy alcohol; mono- or polyunsaturated amides and cycloaliphatic esters of alpha-beta unsaturated carboxylic acids. Examples of such functional crosslinking monomers include polyethylene glycols having a molecular weight up to about 5000 dimethacrylate, triethylene glycol dimethacrylate, tetraethylene glycol dimethacrylate and trimethylol propane ethoxylated triacrylate, available under the trademark CHEMLINK 176, ditrimethylol propane dimethacrylate; propylene, dipropylene and higher propylene glycols having a molecular weight up to about 5000 including polyethylene glycol dimethacrylate, 1,3 butylene glycol dimethacrylate, 1,4 butanediol dimethacrylate, 1,6 hexanediol dimethacrylate, neopentyl glycol dimethacrylate, pentaerythritol dimethacrylate, dipentaerythritol dimethacrylate, bisphenol A dimethacrylate, divinyl (trivinyl) benzene, divinyl (trivinyl) toluene, triallyl maleate, triallyl phosphate, diallyl maleate, diallyl itaconate, and allyl methacrylate.

The monofunctional monomer of the novel polymeric system includes hydrophobic and hydrophilic monounsaturated monomers. The monomers include styrene and alkyl methacrylates and acrylates having straight or branched chain alkyl groups with 1 to 30 carbon atoms, preferably 5 to 18 carbon atoms. Preferred monofunctional monomers include styrene, lauryl methacrylate, 2-ethylhexyl methacrylate, isodecylmethacrylate, stearyl methacrylate, hydroxy ethyl methacrylate, hydroxy propyl methacrylate, diacetone acrylamide, phenyl ethyl methacrylate, tetrahydrofurfuryl mathacrylate and methoxy ethyl methacrylate.

The structure of the crosslinked polymer is characterized by a layered ordering of the side chains.

The side chains separated by the backbone chains are packed in parallel layers. The backbone chains of the macromolecules are spaced by distances roughly equal to the length of the side chain.

Dependent on the structure of the linkage of the side chain to the main backbone chain, the degree of conformation freedom at the side chain junctions varies. While polyalphaolefins do not have conformational freedom of the side chain segments around the C—C bond, polyacrylates and polyvinyl ethers have greater degree of freedom due to the C—O bond. The freedom of rotation of the polymethacrylates is limited by the stearic hindrance of the methyl group in the backbone chain.

The crosslinking monomer, monofunctional monomer and functional material are combined in a ratio such that the resultant novel lattice-entrapped composition of this invention comprises from about 5% to about 95% by weight of a crosslinked polymer lattice and from about 95% to about 5% by weight of the entrapped functional material. The ratio of crosslinking monomer to monofunctional monomer in the crosslinked polymer lattice can vary within the range of 99:1 to 1:99. While not restricting the invention to any precise composition, in a typical product of this invention, the crosslinking monomer, monofunctional monomer and functional material are combined in a ratio such that the resultant novel crosslinked polymer lattice comprises from about 60 to about 80% by weight of the functional monomer entrapped therein.

Polymerization may be induced by conventional initiators such as peroxides and the like, or by irradiation or redox systems. Polymerization usually occurs at temperatures between about 0° to 120° C., preferably about 80° C. The time and temperature of polymerization may be varied in accordance with the nature of the functional material, its concentration, and the attributes of the desired entrapped system, but in all instances, the polymerization occurs only after the monomers and the functional material are combined.

PREPARATION OF FOAM

The foams which may be utilized in the invention may be formulated so as to be flexible, semi-rigid or rigid in nature. The foams of the invention can take the form of mop heads, sponges, convoluted pads, seat pads, vaginal devices, inserts in diapers, and the like.

The polyurethane foams employed in the present invention are preferably prepared from a capped polyoxyethylene polyol reactant, having a defined average reaction functionally greater than two, which is mixed with an aqueous reactant. The foams thus generated are characterized by a crosslinked non-linear, molecular network.

The polyoxyethylene polyois used in the preparation of the capped product to be foamed in accordance with the present invention have an average molecular weight of from about 200 to about 20,000 preferably between about 600 and about 6,000 with a hydroxyl functionality of 2 or greater preferably from about 2 to about 8.

The polyoxyethylene polyol is capped by reaction with a polyisocyanate. The capping reaction can be carried out in an inert moisture-free atmosphere, such as under a nitrogen blanket, at atmospheric pressure at a temperature in the range of from about 0° C. to about 120° C. for a period of time ranging up to about 20 hours, depending upon the temperature and the degree to which the reaction mixture is agitated. The capping reaction can also be carried out under ambient conditions so long as the product is not exposed to excess moisture.

The capping is effected using stoichiometric amounts of reactants. It is desirable, however, to use an excess of polyisocyanate in order to insure complete capping of the polyol. The ratio of isocyanate groups to hydroxyl groups is generally between about 1 to about 4 isocyanate groups per hydroxyl group.

The polyisocyanates employed in the capping reaction include (a polyaryl polymethylene polyisocyanate as defined in U.S. Pat. No. 2,683,730), benzene 1,3,5-triisocyanate; chlorophenyl diisocyanate; diphenyl-2,4,4'-triisocyanate; diphenylmethane-4,4'diisocyanate; 3,3'-dimethoxy-4,4'biphenylene-diisocyanate; 3,3'-dimethyl-4,4'biphenylene diisocyanate; dicyclohexylmethane-4,4'-diisocyanate; ethylene diisocyanate; 1,6-hexamethylene diisocyanate; isophorone diisocyanate; 4,4'-methylene-diortho-tolylisocyanate; 4,4'-methylene-bis-(phenylisocyanate); naphthalene-1,5-diisocyanate; tolyene diisocyanate; triphenymethane-4,4'4"-triisocyanate; toluene-2,4,6-triisocyanate; 2,2'5,5'-tetramethyl-4,4'-biphenylene diisocyanate; 2,2',4-trimethyl-1,6-hexane diisocyanate; trimethylenediisocyanate; 4,4'-sulfonylbis (phenylisocyanate); xylene diisocyanate; xylene alphia; 3,3'-dimethyl-4,4'-biphenylene diisocyanate, and the like.

The readily available aromatic diisocyanates, aliphatic and cycloaliphatic diisocyanates and polyisocyanates or mixtures thereof, having a high degree of reactivity, are suitable for use in the capping reaction.

The preparation of the prepolymers, isocyanate-capped polyoxyethylene polyol reaction products, employed in the present invention may follow any one of several methods such as set out in U.S. Pat. No. 4,137,200.

Blends or mixtures of various polyols and isocyanates may be used as desired so long as the total average isocyanate functionality of the final prepolymer is greater than 2.

One method of preparing the prepolymer is by reacting polyoxyethylene glycol having a reactive functionality equal to 2 with a molar excess of a diisocyanate which leads to an isocyanate-capped polyurethane intermediate product having an isocyanate functionality of 2. Similarly, a polyol such as pentaerythritol having a reactive functionality equal to 4 is reacted with a large excess of a diisocyanate to form an isocyanate-capped polyurethane intermediate having an isocyanate functionality of 2 with the intermediate having an isocyanate functionality of 4, in various molar proportions; the resulting mixtures have an average isocyanate functionality of at least 2 and on treatment with aqueous reactants in the presence of a cationic germicidal and antiviral agent will lead to the novel structures of the present invention. Additionally, other monomeric or polymeric polyisocyanate crosslinking agents may be substituted for the isocyanates employed; thus use for instance of tolylene-2,4,6-triisocyanate having a reactive functionality of 3 is an example of a simple monomeric triisocyanate which may be usefully employed to achieve the same objective of imparting to the system an average isocyanate functionality greater than 2.

To effect foaming and the preparation of the novel foam structure of the present invention, the capped prepolymer is simply combined with a particular aqueous component. In the case of the present invention, the aqueous component may appear as a water solution with discrete particles of a polymer having functional material entrapped within the polymer lattice distributed therein.

EXAMPLE I

Preparation of Bacterial Agent Entrapped in Polymer 1.20 grams of polyvinyl pyrrolidone having a K value of about 80 to 100 and available from Dan River, Inc., was dissolved in 1500 ml of water in a 2000 ml three necked resin flask equipped with a stirrer, thermometer and nitrogen purge. 335 grams of glutaraldehyde, 132 grams ethylene glycol dimethacrylate, 33 grams 2-ethylhexyl methacrylate and 5 ml t-butyl peroctoate was bubbled with nitrogen for 5 minutes. The resultant monomer mix was slowly added to the stirred aqueous solution of polyvinyl pyrrolidone a 22° C. under nitrogen. The temperature was raised to 80° C. with constant agitation and held until polymerization started in approximately 15 minutes, and maintained at 80° C. for an additional 2 hours to complete the reaction. Semi-soft, white opaque beads were collected by filtering off the supernatant liquid and dried to remove any excess water. The beads were about 0.25 to 0.5 mm in diameter.

Other protective colloids such as starch, polyvinyl alcohol, carboxymethyl cellulose, methyl cellulose, or inorganic systems such as divalent alkali metal hydroxides, for example MgOH, may be used in place of the polyvinyl pyrrolidone suspending medium.

In lieu of the bacterial agent, glutaraldehyde, there may be utilized pharmaceutical agents such as iodine solutions, triamcinolone, hydrocortisone, and the like.

EXAMPLE II

Preparation of Fragrance Entrapped in Styrene-divinylbenzene Copolymer

A 4.0 liter polymer kettle containing 200 ml of distilled water and 200 ml of pine oil is flushed with nitrogen. The solution is mixed and the temperature is raised to approximately 85° C. To the kettle is rapidly added 500 ml of a monomer comprising 20 percent by weight divinylbenzene, 5 percent by weight benzoyl peroxide and the remainder being styrene. After 30 minutes the polymerization was ended and semi-soft beads of polymer entrapped pine oil was collected by filtration.

Other similar products are commercially available from Wickhen Products, Inc., Huguenot, N.Y. 12746 under the trademark POLYTRAP.

Typical examples of other fragrances which may be used includes lemon oil, strawberry, orange oil, anethole, citral, biacetyl, menthol, anise, amyl acetate, ethyl acetate, lavender oil, blue spruce, apple, spearmint, peppermint, spice mint, peach, attar of roses, apple (International Flavors and Fragrances #58125), pine (IFF 4276-X), spearmint (IFF V 30549), lime (IFF 3117 W), spice-mint (Gentry #401283-00), carnation-peach (Gentry #401186-00), lemon-verbenna (Ungerer C-454), soap fragrance (Roue Bertrand DuPont D 723), melon (American Aromatics #12), (Felton International): floral bouquet #221, leather musk bouquet #323, cream bouquet #800, rose bouquet #593A, green apple bouquet #503, pine bouquet #740A, strawberry #863.

There can also be added bacterial agents, e.g., benzalkonium chloride, disinfecting agents, insect repellants, e.g., N,N-diethyl-m-toluamide, pyrethrum flowers, etc.

Additionally, there can be added soluble or insoluble dyes and pigments, e.g., FD&C yellow #5, D&C Red #9 (Thomasset Colors) D&C mint green (Pylam Products Co.), mercadium red light GP (hercules), C.P. medium yellow (Hercules), titanium dioxide (Unitane-American Cyanamide), carbon black (Konstamm).

EXAMPLE III

Preparation of Polymer Entrapped Pesticide

Six parts of 2-hydroxyethyl methacrylate, six parts of n-acrylamide and eight parts of dimethacrylate were intimately mixed with ten parts of Diazinon (0.0 diethyl-0-(2-isopropyl-4-methyl) thiophosphate), 0.5 part of benzoyl peroxide and 0.5 part of dimethyl-p-toluidine. The mixture was deaerated in vacuo and bubbled with nitrogen for three minutes. Polymerization was conducted at 80° C. A soft opaque gel was obtained.

The polymerization can also be performed utilizing a synthetic pheromone alone or in combination with the pesticide. Suitable pheromones include t-butyl-4-(or 5) chloro-2-methyl cyclohexane carboxylate (Tumedlure), alpha-pinene, 3,4-dimethoxy-allylbenzene (methyl Eugenol), Z-9 Tucosene (Muscalure), and the like.

EXAMPLE IV

An anti-viral and germicide containing foam is prepared according to the process of U.S. Pat. No. 4,339,550 as follows: 25 g. of isocyanate-capped polyoxyethylene polyol is combined with 75 g. of an aqueous reactant mixture. The aqueous reactant mixture is comprised of 28 g. of water, 24 g. of the beads from Example I and 1.5 g. of Pluronic L-64. The polyoxyethylene polyol and aqueous reactant are mixed together to obtain a homogenous mixture. Immediately after homogenity is obtained the mixture is poured into a suitable mold. The resulting foam is cured in about 10 minutes at ambient temperature.

The foam can be utilized as a sponge or a mophead for sterilizing hospital rooms. If the foam is dried, the anti-viral and germicidal agent can be released by dipping the foam in an aqueous medium so as to release the entrapped active ingredients.

The foam as a bed pad provides a sustained release of odorant and availability of sterilizing agent for use with bed-ridden patients in order to help in preventing decubitus and to alleviate odors resulting from bacteria.

Addition of small amounts of the beads of Example II can also be added, about 1–5%, so as to provide an odorant.

EXAMPLE V

Preparation of Novelty Yarn

A 100-filament yarn was prepared according to the method set forth in U.S. Pat. No. 2,914,376 of Bibolot et al by spinning an aqueous dispersion of 75% styrene, 5% butadiene and 20% of particles of a fragrance entrapped in a hydrophilic crosslinked polymer (styrene-divinylbenzene). The resulting fibers can either be used singly or constructed into a fabric having a lingering fragrance.

EXAMPLE VI

A mixture of finely ground sulfonated styrene-divinylbenzene polymer containing 15% divinylbenzene and polyethylene pellets was heated to 180° C., kneaded in a mixture and pelletized to 1/16" pellets. The pellets were fed to a screw extruder. Prior to extrusion into 1 mil sheet, particles of insecticide entrapped styrene-divinylbenzene beads prepared according to Example II were added. The resulting sheet was cut into strips for use as animal collars or for use in homes and restaurants as insecticidal strips.

The discrete particles containing functional material can be incorporated into a wide variety of plastic materials utilizing any one of the conventional methods such as disclosed in *Modern Plastics Encyclopedia*, 1984–85, McGraw-Hill, Vol. 61, No. 10A, which is incorporated herein by reference.

Having thus described the invention with reference to the particular forms thereof, it will be obvious to those skilled in the art to which this invention pertains, that changes and modifications can be made without departing from the spirit and scope of the invention as defined by the appended claims.

What is claimed is:

1. A plastic composition having a functional material suited for performing a specific function when said functional material is released from said plastic composition, which plastic composition comprises: a thermoplastic polymeric substrate selected from the group consisting of polyurethane, polyolefin, polyvinyl chloride, acrylic and cellulose, and a crosslinked polymer having said functional material trapped within its polymer lattice, the crosslinked polymer selected from the group consisting of a polymer of styrene and divinylbenzene and a polymer of di and triacrylate esters, said crosslinked polymer being present as discrete particles within said thermoplastic polymeric substrate.

2. The plastic composition of claim 1 wherein said discrete particles comprise from about 5% to about 95% by weight of a crosslinked polymer lattice and from about 95% to about 5% by weight of entrapped functional material.

3. The plastic composition of claim 2 wherein said discrete particles comprise a crosslinked polymer which is styrene-divinylbenzene and an entrapped functional material.

4. The plastic composition of claim 1 wherein the thermoplastic polymeric substrate is a polyolefin and the crosslinked polymer is a polymer of styrene and divinylbenzene containing one of a biocide and a pesticide as the functional material.

* * * * *